United States Patent [19]
Nelson et al.

[11] Patent Number: 5,787,188
[45] Date of Patent: Jul. 28, 1998

[54] METHOD FOR IDENTIFYING NORMAL BIOMEDICAL SPECIMENS

[75] Inventors: Alan Caril Nelson, Redmond; Shih-Jong James Lee, Bellevue; Richard S. Johnston, Issaquah, all of Wash.

[73] Assignee: NeoPath, Inc., Redmond, Wash.

[21] Appl. No.: 571,686

[22] Filed: Dec. 13, 1995

Related U.S. Application Data

[63] Continuation of Ser. No. 838,064, Feb. 18, 1992, abandoned.

[51] Int. Cl.$^6$ ............................................. G06K 9/00
[52] U.S. Cl. ................................................ 382/133
[58] Field of Search .............................. 382/133, 134; 356/39; 128/922

[56] References Cited

U.S. PATENT DOCUMENTS

| | | | |
|---|---|---|---|
| 3,919,530 | 11/1975 | Cheng | 235/151.3 |
| 4,097,845 | 6/1978 | Bacus | 382/6 |
| 4,175,860 | 11/1979 | Bacus | 356/39 |
| 4,199,748 | 4/1980 | Bacus | 340/146.3 CA |
| 4,213,036 | 7/1980 | Kopp et al. | 382/6 |
| 4,513,438 | 4/1985 | Graham et al. | 382/6 |
| 4,661,913 | 4/1987 | Wu et al. | 382/133 |
| 4,965,725 | 10/1990 | Rutenberg | 364/413.1 |
| 4,998,284 | 3/1991 | Bacus et al. | 382/6 |
| 5,086,476 | 2/1992 | Baens | 382/133 |
| 5,134,662 | 7/1992 | Bacus et al. | 382/6 |

OTHER PUBLICATIONS

Tanaka, et al., "Cybert Model 3 Automated Cytologic Screening System for Uterine Cancer Utilizing Image Analysis Processing"; Dec. 1982, pp. 279–285.

*Primary Examiner*—Jack B. Harvey
*Assistant Examiner*—Xuong Chung-Trans
*Attorney, Agent, or Firm*—Hans I. Sun; Emil Moffa

[57] ABSTRACT

Method and apparatus for identifying normal biomedical specimens. Image data is gathered representing an image of the specimen. The image data is processed to measure features of the objects to determine whether the object is normal. The feature measurements for all objects in the specimen are then combined to determine whether the specimen as a whole is normal.

20 Claims, 4 Drawing Sheets

METHOD FOR IDENTIFYING NORMAL BIOMEDICAL SPECIMENS

This is a continuation of application Ser. No. 07/838,064, filed on Feb. 18, 1992 now abandoned.

TECHNICAL FIELD

The present invention is directed toward a method for analyzing data representing the image of biomedical specimens and, more particularly, a method for analyzing data representing the image of biomedical specimens to identify normal (negative) biomedical specimens.

BACKGROUND OF THE INVENTION

With increasing progress in data processing technology, both hardware and software, biomedical imaging systems are becoming more and more prevalent. Presently, image gathering systems have been developed for providing images of human anatomy such as, for example, magnetic resonance imaging devices, ultrasound imaging, computer tomography imaging, etc. Image enhancement systems are typically used for processing data to be used to provide an improved image of organs of a patient, as for example, the patient's heart, lungs, etc. However, image enhancement systems make no attempt to diagnose the biomedical status of the functional systems of the patient.

Other image analysis systems have been developed for analyzing image data of specimens taken from a patient to augment the physician diagnosis of the biomedical status of the patient. As examples, image analysis systems have been provided for obtaining image data representing blood cells, bone marrow cells, brain cells, etc. Image analysis systems are typically designed to process image data to determine characteristics of the specimen, as for example, blood cell count. Although these systems make some attempt to analyze the collected data, these systems have not been used significantly to diagnose the overall quality or condition of the specimen, e.g., as either normal (negative) or abnormal. Conversely, these systems have been used primarily as prescreening systems to identify those portions of a specimen that require further inspection by a human.

As an example, image analysis systems have been provided to screen portions of a cervical Pap smear. These systems typically require special (nonstandard) preparation for the cervical Pap smear specimen before the specimen can be examined. This is because a typical cervical Pap smear specimen, that may be examined by a cytotech without the aid of an imaging system, includes layers and chunks of cells that cannot readily be imaged using available data processing technology. However, the special preparation required for these image analysis systems adds an additional step in the preparation and, therefore, increases the overall expense and complexity of the analysis.

Still further, image analysis systems presently available for performing image screening identify objects residing on the slide that do not appear to be normal objects of the specimen. For example, such a device constructed for performing cervical Pap smear analysis would display objects that do not appear to be regular cells, e.g., irregular cells or artifacts. These irregular cells and artifacts are then indicated to a cytotech who must further examine the slide to determine whether the specimen residing on the slide is normal or abnormal. Pre-screening the slides in this manner enables the cytotech to quickly locate the cells that must be examined in detail, since the cytotech is not required to examine the entire slide. However, using this procedure, the cytotech is still required to examine each and every slide. Further, since hundreds of objects may reside on a slide that appear abnormal, the work required of the cytotech to review each and every slide remains substantial. Accordingly, although these image screening systems may reduce the time required for the cytotech to locate irregular cells and artifacts, they are nonetheless undesirable since they do not provide a substantial reduction in the amount of examination of irregular cells and artifacts required by the cytotech to determine if a specimen is normal or abnormal.

Accordingly, it is desirable to provide an image analysis system that is capable of analyzing data representing an image of a biomedical specimen. Further, it is desirable to provide an image analysis system that is capable of analyzing data representing an image of a specimen wherein the image analysis system is able to determine the overall condition of the specimen. Still further, it is desirable to provide an image analysis system for analyzing biomedical specimens wherein the image analysis system is capable of determining whether a group of cells that do not appear normal represent a normal or abnormal specimen, and ultimately to determine whether the specimen as a whole is normal.

SUMMARY OF THE INVENTION

The present invention provides a method for analyzing data representing the image of a biomedical, or other, specimen. The method includes the step of processing the image data to identify objects of the images and provide object data wherein the object data represents the objects identified. The method further includes the step of analyzing the object data to determine the measurement of predetermined features of the objects represented by the object data. The feature measurements are used to obtain a confidence factor for each object wherein the confidence factor indicates the probability that the object is normal with respect to the predetermined features and is used therefore to classify the objects as normal or abnormal. Finally, the method includes the step of combining the confidence factors for all objects of the specimen to provide an overall rating for the specimen and determining whether the overall rating is within a predetermined range and, if so, identifying the specimen as normal.

In a presently preferred embodiment of the invention, the object data is analyzed by examining the objects located proximate a subject object to provide feature measurements and confidence factor for the subject object that is determined by the characteristics of objects located proximate the subject object. In still another alternative embodiment, the objects located proximate the subject object are examined by providing a neighborhood feature measurement and a numbers feature measurement wherein the neighborhood feature measurement is indicative of the features of the objects surrounding the subject object and wherein the numbers feature measurement is indicative of the number of objects located proximate the subject object.

DETAILED DESCRIPTION OF THE INVENTION

Figure 1:
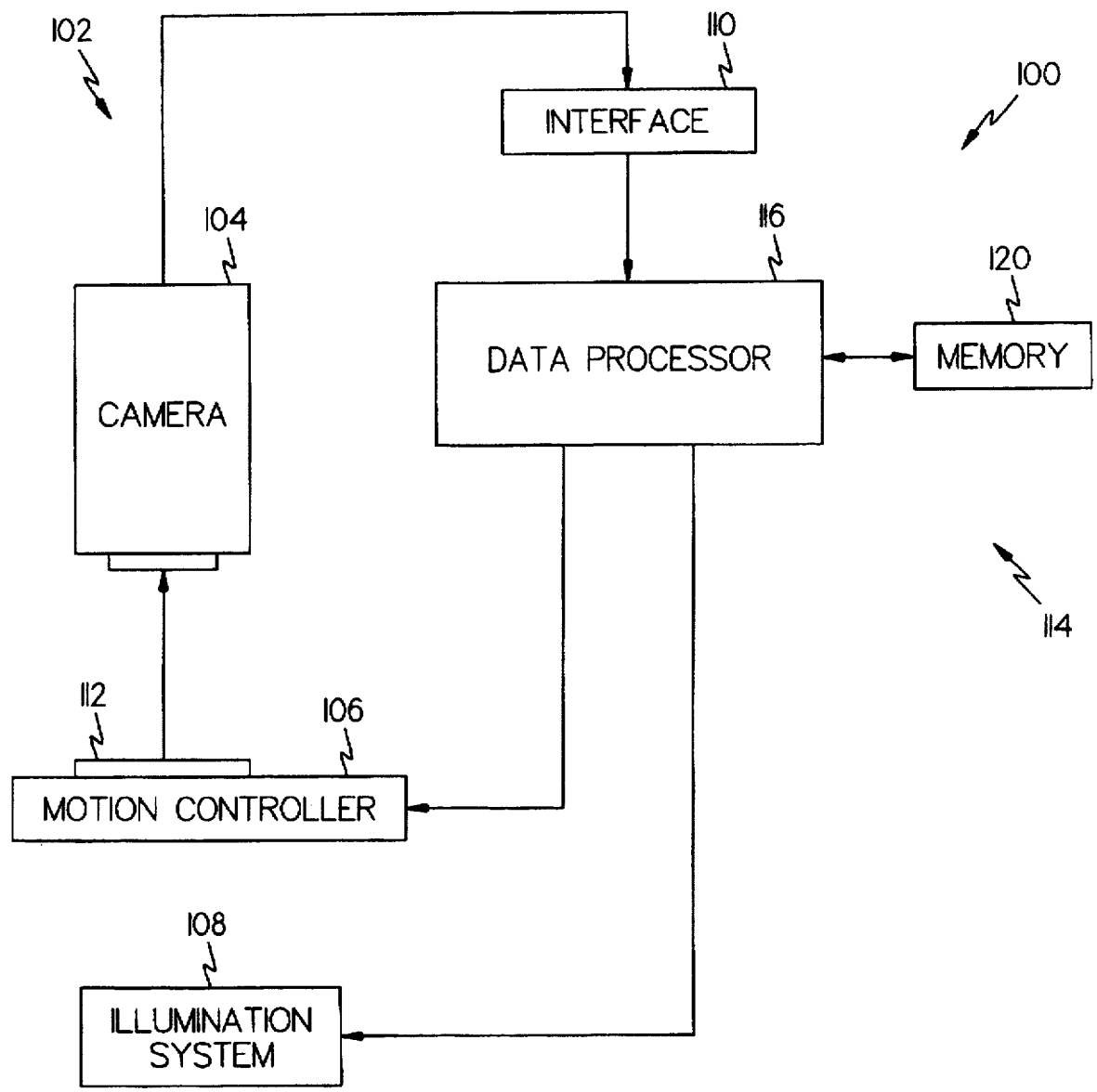
FIG. 1 is an illustrative block diagram of an image analysis system constructed in accordance with the subject invention.

An image gathering and analysis system 100 is illustrated in FIG. 1. The image analysis system is provided for gathering and analyzing data representing the image of a biomedical specimen, to identify normal biomedical specimens. In a presently preferred embodiment of the invention, the image gathering and analysis system 100 is constructed for analyzing images representing a cervical Pap smear specimen residing on a microscope slide. Those skilled in the art will recognize that the method of the subject invention is applicable to all biomedical analysis, including monolayer preparations. Still further, those skilled in the art will recognize that the present invention could be used in combination with analysis of biomedical specimens in various other fields of cytology and histology. As examples, the subject invention could be readily constructed for use with blood samples, urine samples, feces samples, sputum samples, skin scrape samples, etc. Further, the present invention could be used for histology analysis such as, for example, biopsies, tissue chunks, or other bulk biomedical samples. Still further, the present invention can be applied to various other imaging systems such as, image enhancement system, or scientific image analysis systems.

The image gathering and analysis system 100 includes an image gathering system 102 comprising a camera 104, a motion controller 106, an illumination system 108, and an interface 110. The image gathering system 102 is constructed for gathering image data representing an image of a specimen mounted on a slide 112. The image data collected typically includes a plurality of data words wherein each data word is associated with a pixel of the camera 104 and wherein each data word is a multiple bit binary word having a binary value that indicates the transmissivity of a respective portion of the specimen.

The camera 104 is constructed for providing the image data to an interface 110 that captures the image data and prepares the image data for use by the image analysis system 100. The motion controller 106 is responsive to the image gathering and analysis system 100 for positioning the slide 112 so that the camera 104 can provide image data representing different fields of view of the slide 112. In a presently preferred embodiment of the invention, the motion controller 106 is constructed to provide as many as 15,000 field of view images for each slide 112.

The illumination system 108 is provided for illuminating the slide 112 to increase the grayscale content and speed of the image data provided by the camera 104. As mentioned above, the present invention is preferably constructed to be effectively used without the need to provide special nonstandard preparation to the specimen on the slide 112. To this end, the image gathering system 102 is constructed for precision focusing of a substantially three-dimensional object mounted on the slide 112. Suitable apparatus for capturing images in accordance with the present invention is shown and described in U.S. patent application Ser. No. 07/838,073, for *Method and Apparatus for Rapid Capture of Focused Microscopic Images*, by Jon W. Hayenga et al, filed Feb. 18, 1992, and U.S. patent application Ser. No. 07/838,065, entitled *Method and Apparatus for Dynamic Correction of Microscopic Image Signals*, by Jon W. Hayenga et al, filed Feb. 18, 1992, both disclosures of which are incorporated herein, in their entireties, by the foregoing references thereto.

The image gathering system 102 is coupled to a data processing system 114 for providing the image data thereto. The data processing system 114 is constructed for analyzing the image data to identify slides containing only normal biomedical specimens, as will be described in more detail below. Notably, the data processing system 114 is constructed to identify objects that may appear abnormal, as is done by prior art image screening devices. However, the data processor 114 is further constructed to analyze the plurality of objects that appear abnormal on the slide 112 to determine whether the specimen on the slide 112 is actually normal or abnormal. Accordingly, the data processing system 114 is capable of determining that specimens, which may contain objects that appear abnormal, are nonetheless normal biomedical specimens.

The data processing system 114 includes a data processor 116 coupled to a memory 120. The memory 120 is constructed for storing program data and instructions for use by the data processor 116 in performing the image analysis method discussed in more detail below. Further, the memory 120 may be provided for storing the image data provided by the interface 110 in addition to intermediate analysis data. As an example, analysis of a field of view image typically requires that the image data representing the field of view image be converted to a form distinct from that provided by the image gathering system 102. The memory 120 must be substantial to store the data representing a number of fields of view and also to store intermediate data for each field of view.

The data processor 116 may comprise any of a plurality of commercially available devices for performing data processing on image data. In a presently preferred embodiment of the invention, the data processor 116 comprises a plurality of image processor boards in combination with standard microprocessor circuits, for performing parallel and pipeline image analysis functions. Suitable apparatus for use as the data processor 116 is shown and described in U.S. patent application Ser. No. 07/838,070, entitled *Method and Apparatus for Rapidly Processing Data Sequences*, by Richard S. Johnston et al, filed Feb. 18, 1992, the disclosure of which is incorporated herein, in its entirety, by the foregoing reference thereto.

Figure 2:
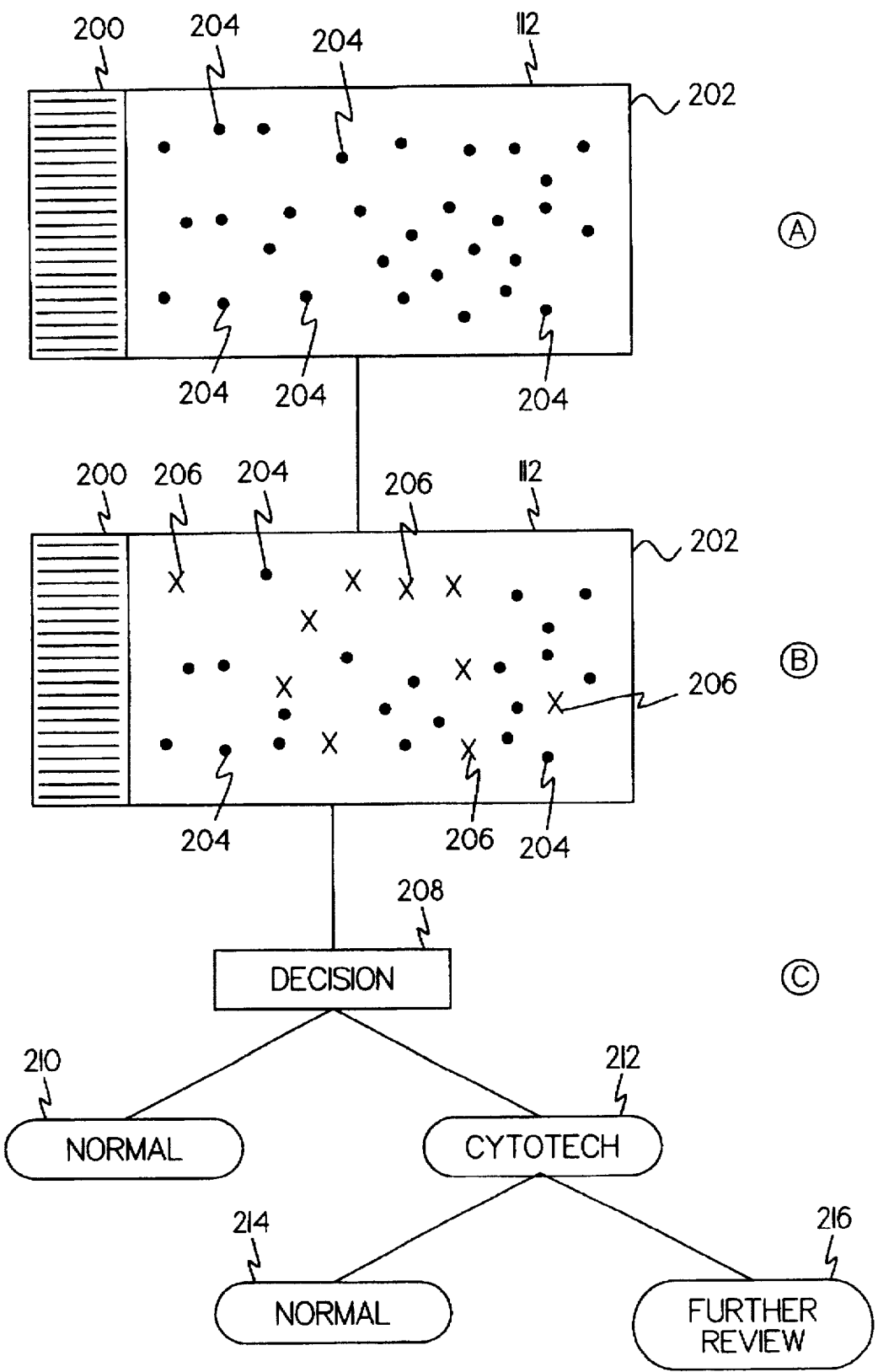
FIG. 2 is a diagram illustrating the general methodology of the method of the subject invention.

The image gathering and analysis system 100 represents an improvement over prior art image screening systems since the image analysis system is capable of determining whether the specimen as a whole is normal. In contrast, prior art image screening systems are only capable of identifying acceptable objects that may appear on a slide. With reference to FIG. 2, the slide 112 may include a bar code portion 200 having a bar code or other machine readable identifier positioned thereon, and a specimen portion 202 upon which the specimen is mounted. As illustrated in step A of FIG. 2, the specimen may include a plurality of objects 204. Prior art devices for performing image prescreening are constructed to capture data representing the image of the objects 204 on the slide 112 and to analyze the captured image data to identify objects 206 (step B) that do not appear normal. These prior art devices can store the recorded images of the located objects for review on a CRT by the cytotech.

In contrast, the image gathering and analysis system 100 of the subject invention goes beyond the steps A and B to analyze the image data representing the objects 206 and to make a decision, as illustrated at step 208, as to whether the specimen mounted on the slide 112 is normal. If the slide is normal, step 210, the cytotech need not examine the slide. If, however, decision 208 does not decide that the slide is normal, it is analyzed by the cytotech, step 212, for an independent opinion of whether the slide is normal, step 214, or whether the slide requires further review, step 216.

Those skilled in the art will appreciate that the present invention represents a significant improvement over the prior art since the cytotech is not required to review each and every slide or any subject data from each and every slide to make a determination of whether the specimen is normal. Apparatus implementing the subject invention can be constructed to identify as much as 50–80% of the total slides reviewed as normal slides. This represents a respective 50–80% reduction in the work load of the cytotech and, accordingly, the ability to significantly increase throughput of the biomedical analysis laboratory.

Figure 3A:
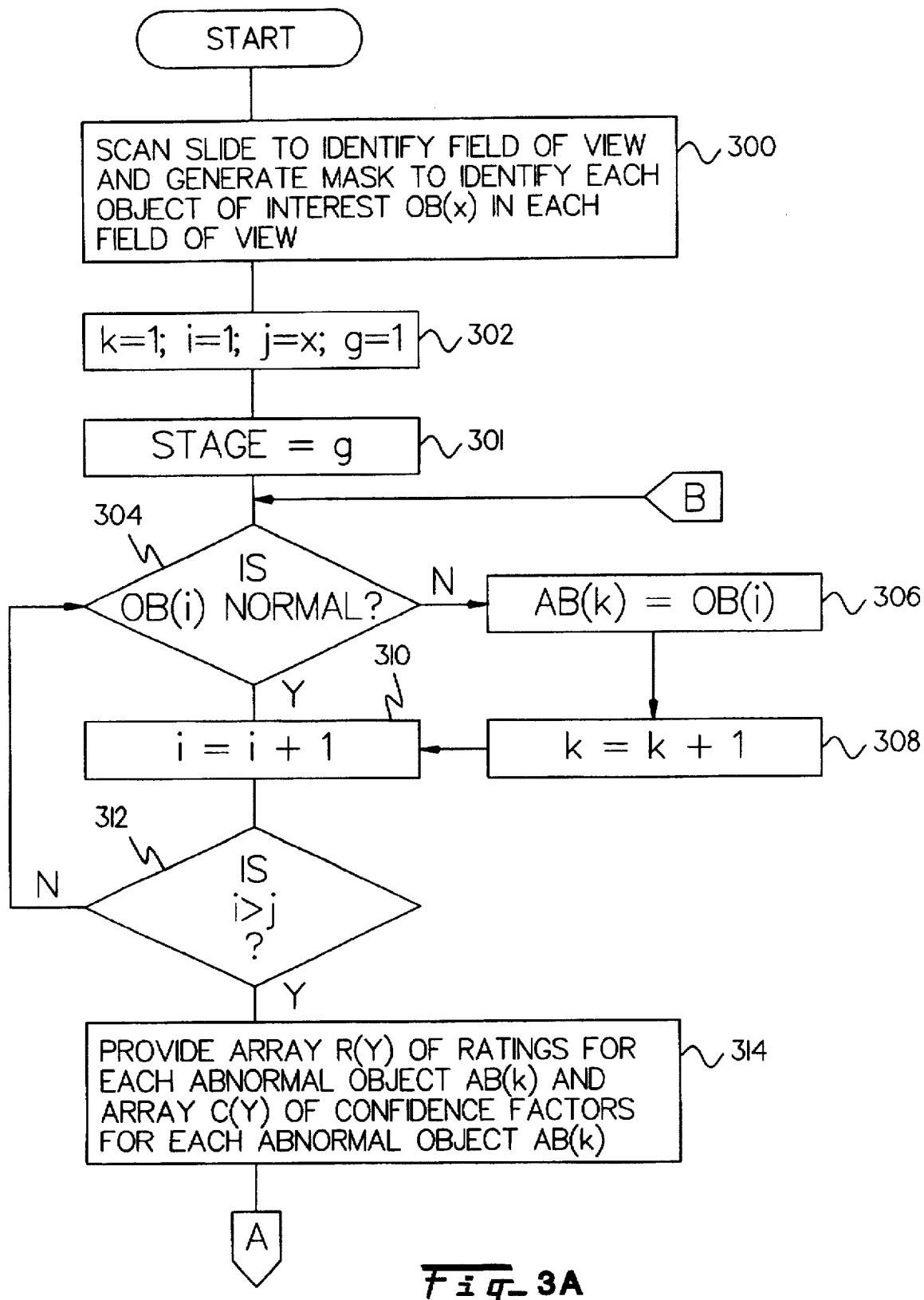
FIGS. 3(*a&b*) is an illustrative flow diagram illustrating in more detail the method of the subject invention.
Figure 3B:
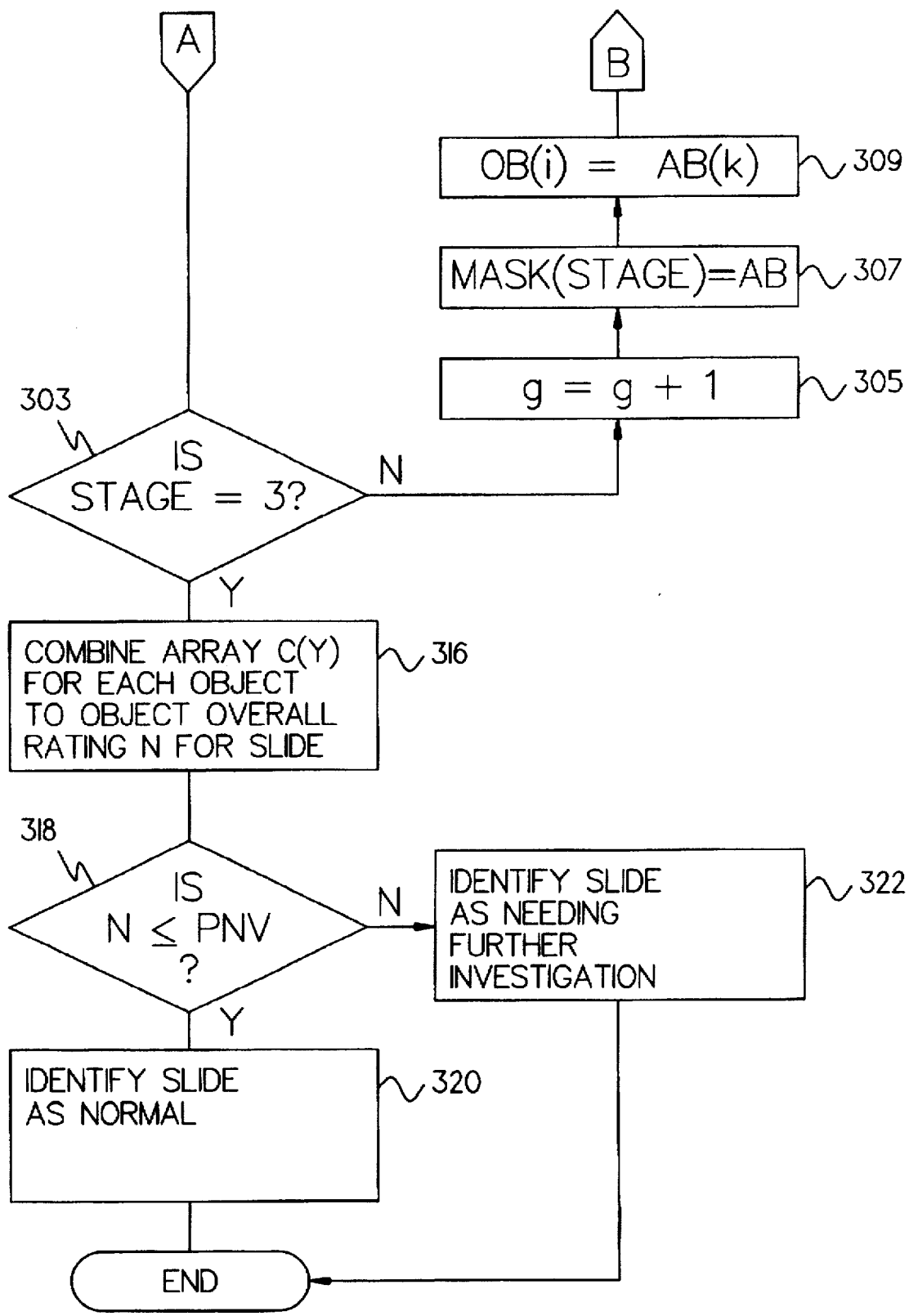

To implement the methodology illustrated in FIG. 2, the present invention performs the method steps illustrated in FIGS. 3A and 3B. Therein, the data processing system 114 provides control signals to the image gathering system 102 (FIG. 1) to scan the slide 112 to provide the image data. The data processing system 114 then processes the image data to identify objects of the specimen on the slide. It will be apparent to those skilled in the art that each object may comprise a cell, a group of cells, or an artifact. In a presently preferred embodiment of the invention, the data processing system 114 controls the image gathering system 102 to scan the slide a first time at a first magnification to determine which fields of view contain objects. The data processing system 114 controls the image gathering system 102 to scan the slide a second time at a higher, second magnification to obtain field of view image data representing the fields of view identified during the first scan. In this fashion, various resolutions of the image data, are obtained.

For each set of field of view image data provided, the data processing system 114 generates a mask to identify each object of interest within the field of view. The mask thus generated includes a number of object identifiers OB(x), so that the mask can be combined with the original field of view data to generate data characterizing each object OB. A suitable method for processing the image data to provide the mask of objects OB(x) is disclosed and described more fully in U.S. patent application Ser. No. 07/838,395, entitled *Method for Identifying Objects Using Data Processing Techniques*, by S. James Lee et al, filed Feb. 2, 1992, the disclosure of which is incorporated herein, in its entirety, by the foregoing reference thereto.

After the mask has been generated to identify the objects OB(x) in the field of view, variables are initiated for use in the method, step 302. The variables k, i, and g are index variables and are initially set equal to 1. The variable j is used to identify the number of objects x in the mask of objects of interest. In the presently preferred embodiment of the invention, the objects of interest are classified in three stages. Accordingly, a variable stage is set equal to g, step 301, to record the present stage of evaluation. The mask of objects of interest OB for the first stage is therefore referred to as a stage mask.

Each object is then examined to determine whether the object appears normal or abnormal, step 304. The determination of whether the object appears normal or abnormal is made by measuring a number of features of the object to characterize the object. Examples of features that may be measured to characterize the object, and thereby determine whether the object is normal include the object size, shape, density, and texture. In a presently preferred embodiment of the invention, wherein the image gathering and analysis system 100 is used for cervical Pap smear analysis, features of neighboring objects are measured to determine whether a subject object is normal. Examples of features of neighboring objects that can be measured are the number of abnormal objects proximate the subject object in addition to the number of total objects proximate the subject object. Additional features of neighboring objects may be measured, in other applications, to determine whether the subject object is normal.

It will be apparent to those skilled in the art that, although certain features have been described herein for use in determining whether a cervical Pap smear cell is normal, other features may be substituted therefor. Further, where the subject invention is applied to other fields of cytology, histology, or other image analysis areas, various other features, and feature combinations, may be desirable to determine whether a given object is normal or abnormal.

Regardless of the features selected, the feature measurements are combined as will be discussed below, and a determination made wherein the object appears normal or abnormal, step 304. If the object appears abnormal, then the image data representing a mask of the object is recorded in an array AB(k), step 306. Thereafter, the index variable k is incremented, step 308. Alternatively, if the object appears normal, step 304, then the index variable i is incremented, step 310, and the variable i is compared to the variable j to determine whether all objects of the mask of objects of interest have been examined, step 312. Steps 304–312 are repeated until all objects have been examined, at which point the array AB(k) includes image data identifying each object in the field of view that did not appear normal.

The image data representing the abnormal objects is used to create a stage 2 mask to identify the size, shape and location of the abnormal objects from the stage 1 mask. Those skilled in the art will appreciate that the stage 2 mask identifying the abnormal objects may be created in number of ways. As examples, the normal objects may be subtracted from the stage 1 mask so that objects identified as being abnormal remain. Alternatively, the stage 2 mask may be created by adding data representing the abnormal objects in the stage 1 mask to a blank mask. As still another alternative, the stage 1 mask may be refined by additional image processing on the original grayscale image to produce the stage 2 mask. Other methods for creating the stage 2 mask will readily become apparent to those skilled in the art.

So that steps 301–312 are repeated for three stages, the variable Stage is compared to three to determine if the third stage has been completed, step 303, and, if not, the index variable g is incremented by 1, step 305, the objects of the stage 2 mask are stored in the object of interest array OB. (FIG. 3B)

In accordance with a presently preferred embodiment of the invention, different features are measured during each sequential stage to determine whether objects are normal or abnormal. As an example, abnormal objects may be identified by measuring their size and shape during stage 1. Any objects identified as abnormal during stage 1 will be measured during stage 2 to determine whether they are actually abnormal. During stage 2, the texture and density of the object may be measured to determine whether the object is normal or abnormal. Any objects identified as abnormal during stage 2 will be measured during stage 3 to determine whether they are normal or abnormal. During stage 3, the number of abnormal objects proximate the subject object and the total number of objects proximate the subject object may be measured to determined whether the object is normal or abnormal.

In determining whether an object is normal or abnormal, in either stage 1, stage 2, or stage 3, the feature measurements for the object are input into a modified binary decision tree wherein the terminal node of the decision tree identifies a region of the feature space used as the decision tree input. Particularly, each terminal node is assigned predetermined confidence values so that if the measurements of an object results in a particular terminal node of the binary tree, the predetermined confidence values are assigned to that object. In the presently preferred embodiment of the invention, each terminal node assigns three confidence values to each object. One value is assigned to indicate the probability that the object is an artifact, another confidence value is assigned to indicate the probability that the object is a normal cell, and a third confidence value is assigned to indicate the probability that the object is abnormal. In a presently preferred embodiment of the invention, the confidence value of the greater magnitude is used to determine whether the object is an artifact, normal cell, or abnormal cell. However, those skilled in the art will appreciate that the confidence values may be compared, combined, or used in various ways to classify the objects as normal, abnormal, or artifacts. Further, it will be apparent that other confidence values may be assigned to provide other or different classifications. Also, although a binary decision tree is used to combine the feature measurements, other data processing methods could be substituted here as well.

In this regard, the objects are classified with respect to features that are related to other objects on the slide in addition to being classified with respect to features such as those discussed above, that are related to the object itself. As an example, an object may receive a neighborhood feature measurement that is related to its neighboring objects. If the objects neighboring the subject object appear abnormal in size or shape, then the neighborhood feature measurement of the subject object will indicate relative abnormalcy. Conversely, if the neighboring objects all appear as normal cells, then the neighborhood feature measurement of the subject object will indicate relative normalcy. Similarly, each object may be given a numbers feature measurement indicating the normalcy of the object by reference to the number of cells neighboring the object. In this regard, if the number of cells neighboring the object are within a predetermined range, then the object will be given a numbers feature measurement indicating relative normalcy. Conversely, if the number of objects neighboring the subject object falls outside the predetermined range, then the object will be given a numbers feature measurement indicating relative abnormalcy.

With respect to the feature measurements provided the plurality of objects AB(k) that do not appear normal, each measurement may vary over a predetermined range so that a range of values can be assigned to the object. Further, those skilled in the art will readily appreciate that other features, both the features relating to the object and features relating to neighboring objects or conditions may be provided in addition to those features discussed herein. However, an important aspect of the subject invention is that not only is the subject object classified in accordance with features relating to the subject object, but the subject object is classified in accordance with features external to the subject object. This allows a more accurate determination of whether the specimen as a whole is normal or abnormal.

Returning to FIGS. 3A and 3B, after stage 3 has been completed, the data processor 116 of the image gathering and analysis system 100 includes classification data for each stage wherein the classification data identifies the number of normal objects identified during that stage, the number of abnormal objects identified during that stage, and the number of artifacts identified during that stage. To make the determination of whether the overall slide appears normal, the classification data is combined to provide an overall rating N for each slide, step 316. The overall rating is then compared to a predetermined normal value PNV and, if the overall rating is less than the predetermined normal value, then the slide is identified as normal, step 320. If, however, the overall rating N is greater than or equal to the predetermined normal value, then the slide is identified as a slide needing further investigation, step 322, and must be reviewed by a cytotech.

The classification data may be combined in a plurality of manners to provide the overall rating N. Similarly, a plurality of normal values, PNV, may be selected wherein the relative magnitude of the normal value will determine, in part, the accuracy of the method. A presently preferred method for combining the classification data to determine whether the slide is normal is to provide two classification factors $f_1$ and $f_2$ wherein the classification factors are defined as follows:

$$f_1 = \frac{\text{No. of stage 3 abnormal objects}}{\text{No. of stage 2 abnormal objects}} \quad (1)$$

and wherein $$f_2 = \frac{\text{No. of stage 3 abnormal objects}}{\substack{\text{No. of stage 1 normal objects +} \\ \text{No. of stage 2 normal objects +} \\ \text{No. of stage 3 normal objects}}} \quad (2)$$

The overall rating N for the slide is then defined as an anomaly score as follows:

$$\text{anomaly score} = \Omega_1 f_1 + \Omega_2 f_2 \quad (3)$$

wherein ($\Omega_1$ and $\Omega_2$ are predetermined constants.

It will be apparent to those skilled in the art that the classification data may be combined in a number of ways to determine the overall rating for the slide. As examples, the number of normal objects for each stage may be compared to the number of artifacts and/or the number of abnormal objects. As another example, the number of abnormal objects for the various stages may be compared to the number of normal objects for the various stages. Still further, the confidence factors may be used in combination with the classification data to provide the overall rating for the slide. Those skilled in the art will appreciate that a wide variety of ways of combining the classification data and the confidence factors to provide an overall rating for the slide may be obtained.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. A method for determining a condition of an object on a biological specimen slide having a plurality of other objects, for an image gathering system controlled by a data processing system, the method comprising the steps of:

(a) obtaining at least one image of the object and at least one image of the plurality of other objects with the image gathering system;

(b) measuring at least one feature for at least one of the plurality of other objects with the data processing system;

(c) classifying at least one of the plurality of other objects as either normal or abnormal based on the at least one feature with the data processing system; and (d) classifying the object as normal or abnormal based on a classification of at least one of the plurality of other objects neighboring the object with the data processing system.

2. The method of claim 1 wherein the plurality of other objects further comprise cells, nuclei and artifacts.

3. The method of claim 1 wherein the at least one feature is selected from the group comprising size, shape, density and texture.

4. The method of claim 1 wherein the biological specimen slide comprises a biological specimen taken from a patient, wherein the biological specimen taken from a patient is mounted on a microscope slide.

5. The method of claim 1 wherein the biological specimen slide comprises a cervical Pap smear slide.

6. The method of claim 1 wherein the step of obtaining at least one image of the object and the plurality of other objects with the image gathering system further comprises the steps of:
 (a) obtaining at least one field of view of the object and plurality of other objects with the image gathering system; and
 (b) generating a mask of object identifiers for each one of the at least one field of view to identify the object and plurality of other objects within the at least one field of view.

7. The method of claim 1 wherein the at least one feature is a member of a feature space and wherein the step of classifying at least one of the plurality of other objects as either normal or abnormal based on the at least one feature with the data processing system further comprises the steps of:
 (a) inputing the at least one feature into a modified binary decision tree wherein each terminal node of the modified binary decision tree identifies a region of the feature space with the data processing system; and
 (b) assigning each terminal node a plurality of predetermined confidence values with the data processing system so that if a feature measurement of an object results in selecting a terminal node of the modified binary decision tree, the plurality of predetermined confidence values are assigned to that object.

8. The method of claim 7 further comprising the step of assigning three confidence values to each one of the plurality of other objects with each terminal node wherein one value is assigned to indicate a likelihood that the object is an artifact, wherein a second confidence value is assigned to indicate a likelihood that the object is a normal cell, and wherein a third confidence value is assigned to indicate a likelihood that the object is abnormal.

9. The method of claim 1 wherein the step of classifying the object as normal or abnormal is based in part on the classification of at least one of the plurality of other objects neighboring the object and is based in part on a preliminary classification of the object with the data processing system.

10. A biological specimen screening method for use with an image gathering system controlled by a data processing system, the biological specimen screening method comprising the steps of:
 (a) obtaining at least one image of a biological specimen with the image gathering system;
 (b) identifying a plurality of objects in the at least one image with the data processing system;
 (c) measuring at least one feature for at least one of the plurality of objects with the data processing system;
 (d) classifying at least one of the plurality of objects as either normal or abnormal based on the at least one feature with the data processing system;
 (e) classifying at least one of the plurality of objects as either normal or abnormal based on a classification of at least one other one of the plurality of objects neighboring the plurality of objects with the data processing system; and
 (f) screening the biological specimen as normal based on the classification of at least one of the plurality of objects classified in step (d) and step (e) with the data processing system.

11. The biological specimen screening method of claim 10 wherein the plurality of other objects further comprises cells, nuclei and artifacts.

12. The biological specimen screening method of claim 10 wherein the at least one feature is selected from the group comprising size, shape, density and texture.

13. The biological specimen screening method of claim 10 wherein the biological specimen comprises a biological specimen taken from a patient, wherein the biological specimen is mounted on a microscope slide.

14. The biological specimen screening method of claim 10 wherein the biological specimen comprises a cervical Pap smear.

15. The biological specimen screening method of claim 10 wherein the step of identifying a plurality of objects in the at least one image with the data processing system further comprises the step of generating a mask of object identifiers for each one of the at least one image to identify the plurality of objects within the at least one image.

16. The biological specimen screening method of claim 10 wherein the at least one feature is a member of a feature space and wherein the step of classifying at least one of the plurality of objects as either normal or abnormal based on the at least one feature with the data processing system further comprises the steps of:
 (a) inputing the at least one feature into a modified binary decision tree wherein each terminal node of the modified binary decision tree identifies a region of a feature space with the data processing system; and
 (b) assigning each terminal node predetermined confidence values with the data processing system so that if the measurements of an object result in a particular terminal node of the modified binary decision tree, the predetermined confidence values are assigned to that object.

17. The biological specimen screening method of claim 16 further comprising the step of assigning three confidence values to each one of the plurality of objects with each terminal node wherein one value is assigned to indicate a likelihood that an object is an artifact, wherein a second confidence value is assigned to indicate a likelihood that an object is a normal cell, and wherein a third confidence value is assigned to indicate a likelihood that an object is normal.

18. The biological specimen screening method of claim 10 wherein the step of screening the biological specimen as normal further comprises the step of identifying the biological specimen as requiring no further human review.

19. A biological specimen screening method for use with an image gathering system controlled by a data processing system, the biological specimen screening method comprising the steps of:
 (a) obtaining a plurality of images of a biological specimen with the image gathering system, wherein each one of the plurality of images has at least one field of view;
 (b) identifying at least one object of interest in the at least one field of view with the data processing system;
 (c) measuring at least one feature value of each at least one object of interest with the data processing system;

(d) scoring each at least one object of interest as either normal or abnormal based on the at least one feature value with the data processing system to identify stage one abnormal objects, identify stage one normal objects, count a stage one number of abnormal objects, and count a stage one number of normal objects;

(e) measuring at least one feature value for each of the stage one abnormal objects with the data processing system;

(f) measuring at least one neighborhood feature measurement for the stage one abnormal objects, wherein the at least one neighborhood feature measurement indicates relative stage one abnormality by comparing a size, shape, or density of at least one of the stage one abnormal objects to the size, shape or density of at least one of the objects neighboring the at least one of the stage one abnormal objects;

(g) measuring at least one numbers feature measurement for the stage one abnormal objects, wherein the at least one numbers feature measurement indicates relative stage one abnormality by counting a total number of other stage one abnormal and normal objects that are neighboring the stage one abnormal object;

(h) scoring each stage one abnormal object as either normal or abnormal based on the at least one feature value, the at least one neighborhood feature measurement and the at least one numbers feature measurement with the data processing system, to identify stage two abnormal objects, identify stage two normal objects, count a stage two number of abnormal objects, and count a stage two number of normal objects;

(i) scoring each stage two abnormal object as either normal or abnormal based on a count of a number of abnormal objects proximate the stage two abnormal objects and a count of a total number of objects proximate the stage two abnormal objects with the data processing system, to identify stage three abnormal objects, identify stage three normal objects, count a stage three number of abnormal objects, and count a stage three number of normal objects;

(j) algebraically combining the stage one number of abnormal objects, the stage one number of normal objects, the stage two number of abnormal objects, the stage two number of normal objects, the stage three number of abnormal objects, and the stage three number of normal objects with the data processing system to compute a normal score; and (k) comparing the normal score to a predetermined normal value with the data processing system to screen the biological specimen as normal if the normal score exceeds the predetermined normal value.

20. The biological specimen screening method of claim 19 wherein the step of screening the biological specimen as normal further includes the step of identifying the biological specimen as requiring no further human review.

\* \* \* \* \*

UNITED STATES PATENT AND TRADEMARK OFFICE
CERTIFICATE OF CORRECTION

PATENT NO. : 5,787,188
DATED : July 28, 1998
INVENTOR(S) : Nelson et al.

It is certified that error appears in the above-identified patent and that said Letters Patent is hereby corrected as shown below:

In the Abstract

Line 1, after the word "apparatus" insert -- are disclosed --.

Column 3, line 53, delete serial number "07/838,073" and replace it with -- 07/838,063 --.

Column 5, line 36, delete "Feb. 2, 1992" and replace it with -- Feb. 18, 1992 --.

Column 8, line 28, delete the "(".

Signed and Sealed this

Second Day of February, 1999

Attest:

Attesting Officer

*Acting Commissioner of Patents and Trademarks*